United States Patent
Joe et al.

(10) Patent No.: US 9,708,420 B2
(45) Date of Patent: Jul. 18, 2017

(54) ANIONIC POLYMERIZATION INITIATOR AND METHOD FOR PREPARING CONJUGATED DIENE-BASED POLYMER USING SAME

(71) Applicant: LG Chem, Ltd., Seoul (KR)

(72) Inventors: Dae-June Joe, Daejeon (KR); Min-Soo Kim, Daejeon (KR); Won-Mun Choi, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/125,031

(22) PCT Filed: Oct. 14, 2015

(86) PCT No.: PCT/KR2015/010863
§ 371 (c)(1),
(2) Date: Sep. 9, 2016

(87) PCT Pub. No.: WO2016/099021
PCT Pub. Date: Jun. 23, 2016

(65) Prior Publication Data
US 2017/0015763 A1    Jan. 19, 2017

(30) Foreign Application Priority Data
Dec. 19, 2014 (KR) .................. 10-2014-0184716

(51) Int. Cl.
C08F 4/48 (2006.01)
C08F 2/60 (2006.01)
C08F 236/10 (2006.01)
C07C 211/01 (2006.01)
C08F 136/06 (2006.01)
C08F 112/08 (2006.01)
C08F 236/06 (2006.01)

(52) U.S. Cl.
CPC ............. *C08F 2/60* (2013.01); *C07C 211/01* (2013.01); *C08F 112/08* (2013.01); *C08F 136/06* (2013.01); *C08F 236/06* (2013.01); *C08F 236/10* (2013.01)

(58) Field of Classification Search
CPC .. C08F 4/48; C08F 4/484; C08F 4/486; C08F 4/488
See application file for complete search history.

(56) References Cited

U.S. PATENT DOCUMENTS

| 5,523,364 A | 6/1996 | Engel et al. |
| 5,567,815 A | 10/1996 | Hall et al. |
| 2008/0010346 A1 | 1/2008 | Ratcliff |

FOREIGN PATENT DOCUMENTS

| EP | 0693500 A1 | 1/1996 |
| FR | 2434822 A1 | 3/1980 |
| JP | H0848708 A | 2/1996 |
| JP | 2746053 B2 | 4/1998 |
| JP | 3289977 B2 | 6/2002 |
| KR | 20120139014 A | 12/2012 |
| KR | 101417165 B1 | 7/2014 |

OTHER PUBLICATIONS

Yoshifuji, M. et al., "Preparation and X-Ray Structure of [2,4-di-t-butyl-6-(N,N-dimethylaminomethyl)phenyl]dithioxophosphorane Stabilized by Intramolecular Coordination." Tetrahedron Letters 1994, 35(23), 3971-3974.*
International Search Report for Application No. PCT/KR2015/010863 dated Dec. 28, 2015.
Supplementary European Search Report for Application No. EP15870189 dated Feb. 17, 2017.

\* cited by examiner

*Primary Examiner* — Richard A Huhn
(74) *Attorney, Agent, or Firm* — Lerner, David, Littenberg, Krumholz & Mentlik, LLP

(57) ABSTRACT

Disclosed are an anionic polymerization initiator, which is a reaction product of an organometallic compound and a compound including an alkyl chain having a tertiary amino functional group, and a method of preparing a conjugated diene-based copolymer using the same.

10 Claims, No Drawings

ANIONIC POLYMERIZATION INITIATOR AND METHOD FOR PREPARING CONJUGATED DIENE-BASED POLYMER USING SAME

CROSS-REFERENCE TO RELATED APPLICATION

The application is a national phase entry under 35 U.S.C. §371 of International Application No. PCT/KR2015/010863, filed Oct. 14, 2015, which claims priority to Korean Patent Application No. 10-2014-0184716, filed Dec. 19, 2014, the disclosures of which are incorporated herein by reference.

TECHNICAL FIELD

The present invention relates to a novel anionic polymerization initiator and a method of preparing a conjugated diene-based copolymer using the same.

BACKGROUND ART

Currently, when a copolymer of a conjugated diene monomer and an aromatic vinyl monomer is prepared through typical anionic polymerization, alkyl lithium is used as an anionic polymerization initiator.

In anionic polymerization, a polar solvent such as tetrahydrofuran or dimethylether is generally utilized to prevent aggregation of the initiator and to increase reactivity. For example, JP 2746053 B2 discloses a method of preparing poly(p-tert-butoxy-styrene) using sec-butyllithium as a polymerization initiator and a polymerization solvent comprising tetrahydrofuran. However, this preparation method is disadvantageous because additional equipment is required for the separation process for recovering n-hexane, attributable to the addition of the polar solvent.

Furthermore, butyllithium is problematic upon anionic polymerization because H in the main chain of the polymer is extracted due to high anionic reactivity, undesirably causing side reactions such as the production of branch structures.

DISCLOSURE

Technical Problem

An object of the present invention is to provide an anionic polymerization initiator, which may obviate additional mixing with a polar solvent when initiating anionic polymerization, or which may reduce the use of a polar additive, and a method of preparing a conjugated diene-based copolymer using the same as a monomer initiator for anionic polymerization.

Technical Solution

In order to accomplish the above object, the present invention provides an anionic polymerization initiator, which is a reaction product of an organometallic compound and a compound including an alkyl chain having a tertiary amino functional group represented by Chemical Formula 1 below:

[Chemical Formula 1]

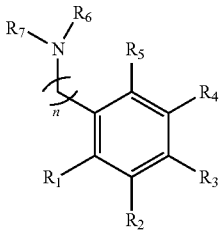

in Chemical Formula 1, $R_1$ to $R_5$ are each independently hydrogen or a C1-C20 hydrocarbon group, two substituents are able to form a single aliphatic or aromatic ring, and at least two of $R_1$ to $R_5$ are alkyl groups; $R_6$ and $R_7$ are a C1-C14 aliphatic hydrocarbon group or a C5-C14 aromatic hydrocarbon group, two substituents being able to form a single aliphatic or aromatic ring when n is 2 or more; and n is 1 to 12.

In addition, the present invention provides a method of preparing a conjugated diene-based copolymer using the anionic polymerization initiator, which is a reaction product of an organometallic compound and a compound including an alkyl chain having a tertiary amino functional group represented by Chemical Formula 1.

Advantageous Effects

According to the present invention, the problems attributable to the mixing with a polar solvent in typical anionic polymerization can be solved, and the initiator can have high activity because of the high ability to dissociate in a non-polar solvent.

According to the present invention, the novel anionic polymerization initiator can reduce the additional use of a polar solvent because a nitrogen atom-containing alkyl group, which is able to coordinate to the lithium cation, is chemically connected to the structure of the initiator.

According to the present invention, the novel anionic polymerization initiator can inhibit side reactions by using a bulky benzyl anion having relatively low reactivity.

According to the present invention, the problems attributable to the mixing with a polar solvent in typical anionic polymerization can be overcome, and high activity can be expected thanks to the high ability of the initiator to dissociate in a non-polar solvent. Furthermore, as at least two alkyl groups are introduced to the benzyl anion, solubility in non-polar solvents can increase, thus making it possible to control the molecular weight of the resulting polymer and the molecular weight distribution (Mw/Mn, MWD) thereof.

According to the present invention, the problems with a solvent separation process, attributable to the mixing with a polar solvent having an ether structure such as tetrahydrofuran or dimethylether, can be solved.

Recently, as silica is mainly used as an environmentally friendly tire reinforcing agent, rubber modification, in which a polar functional group having an affinity for silica is introduced to the conjugated diene-based rubber to efficiently disperse silica, is receiving attention, and thus, the conjugated diene-based rubber using the nitrogen atom-containing initiator according to the present invention can be deemed to increase the dispersibility of the silica reinforcing agent.

BEST MODE

Hereinafter, a detailed description will be given of the present invention.

The present invention addresses an anionic polymerization initiator, produced by reacting an organometallic compound with a compound including an alkyl chain having a tertiary amino functional group represented by Chemical Formula 1 below:

[Chemical Formula 1]

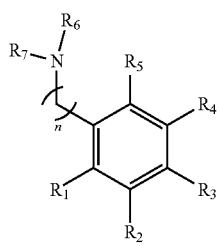

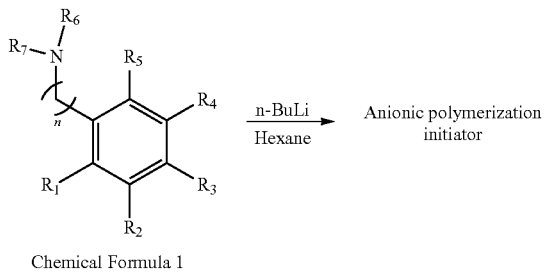

Chemical Formula 1 in Chemical Formula 1, $R_1$ to $R_5$ are each independently hydrogen or a C1-C20 hydrocarbon group, two substituents are able to form a single aliphatic or aromatic ring, and at least two of $R_1$ to $R_5$ are alkyl groups; $R_6$ and $R_7$ are a C1-C14 aliphatic hydrocarbon group or a C5-C14 aromatic hydrocarbon group, two substituents being able to form a single aliphatic or aromatic ring when n is 2 or more; and n is 1 to 12.

The compound represented by Chemical Formula 1 is an organic compound having a nitrogen atom-containing dialkyl group.

Since at least two of $R_1$ to $R_5$ are alkyl groups in Chemical Formula 1, solubility in a non-polar solvent such as n-hexane, which is mainly useful in anionic polymerization, may increase, thus facilitating use as a polymerization initiator.

Preferably, $R_1$, $R_3$, and $R_5$ are methyl, ethyl, and propyl, and most preferably used is methyl. For example, the compound represented by Chemical Formula 1 may be 1-(diethylaminomethyl)-2,4,6-trimethylbenzene or 1-(diisopropylaminomethyl)-2,4,6-trimethylbenzene.

The compound represented by Chemical Formula 1 may be alkylbenzene containing a tertiary amine synthesized by adding bromoalkylbenzene with a primary or secondary amine in the presence of a base, as illustrated in Scheme 1 below. Then, the alkylbenzene containing the tertiary amine is reacted with an organolithium compound such as n-butyllithium, whereby a highly pure initiator is prepared even without additional purification.

[Scheme 1]

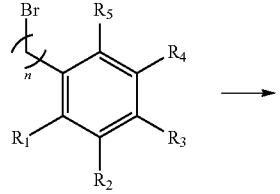

The organometallic compound may be exemplified by an organo-alkali metal compound, or may include at least one selected from the group consisting of an organolithium compound, an organosodium compound, an organopotassium compound, an organorubidium compound, and an organocesium compound.

For example, the organometallic compound may include at least one selected from the group consisting of an organolithium compound, including methyllithium, ethyllithium, isopropyllithium, n-butyllithium, sec-butyllithium, tert-butyllithium, n-decyllithium, tert-octyllithium, phenyllithium, 1-naphthyllithium, n-eicosyllithium, 4-butylphenyllithium, 4-tolyllithium, cyclohexyllithium, 3,5-di-n-heptylcyclohexyllithium, and 4-cyclopentyllithium. Preferably, the organometallic compound is alkyl lithium, such as n-butyllithium, sec-butyllithium or a mixture thereof.

Alternatively, the organometallic compound may include at least one selected from the group consisting of naphthyl sodium, naphthyl potassium, lithium alkoxide, sodium alkoxide, potassium alkoxide, lithium sulfonate, sodium sulfonate, potassium sulfonate, lithium amide, sodium amide, and potassium amide, and may be used in combination with an additional organometallic compound.

According to the present invention, the anionic polymerization initiator obviates the addition of a polar solvent upon anionic polymerization because a monodialkylamino group, which may coordinate to the lithium cation, is chemically connected to the structure of the initiator, and thus the additional use of a polar solvent may be reduced. Furthermore, since the amine group is chemically connected to the structure of the initiator, high activity may be expected due to the high ability to dissociate in a non-polar solvent such as n-hexane.

In addition, the present invention addresses a method of preparing a conjugated diene-based polymer using the anionic polymerization initiator.

More particularly, the method of preparing the conjugated diene-based polymer according to the present invention comprises polymerizing a conjugated diene monomer or a conjugated diene monomer and an aromatic vinyl monomer in the presence of a solvent using an anionic polymerization initiator, which is a reaction product of an organometallic compound and a compound including an alkyl chain having a tertiary amino functional group represented by Chemical Formula 1 below:

[Chemical Formula 1]

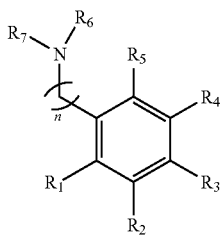

in Chemical Formula 1, $R_1$ to $R_5$ are each independently hydrogen or a C1-C20 hydrocarbon group, two substituents are able to form a single aliphatic or aromatic ring, and at least two of $R_1$ to $R_5$ are alkyl groups; $R_6$ and $R_7$ are a C1-C14 aliphatic hydrocarbon group or a C5-C14 aromatic hydrocarbon group, two substituents being able to form a single aliphatic or aromatic ring when n is 2 or more; and n is 1 to 12.

The conjugated diene monomer may include at least one selected from the group consisting of 1,3-butadiene, 2,3-dimethyl-1,3-butadiene, piperylene, 3-butyl-1,3-octadiene, isoprene, and 2-phenyl-1,3-butadiene.

The aromatic vinyl monomer may include at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. Particularly useful is styrene or α-methylstyrene.

The solvent is not particularly limited, so long as it may be applied in the polymerization or copolymerization of the conjugated diene monomer, and may be exemplified by a hydrocarbon, or may include at least one selected from the group consisting of n-pentane, n-hexane, n-heptane, isooctane, cyclohexane, toluene, benzene, and xylene.

In an embodiment of the present invention, the reaction product of the organometallic compound and the compound including an alkyl chain having a tertiary amino functional group represented by Chemical Formula 1 may be used in an amount of 0.01 to 10 mmol, 0.05 to 5 mmol, 0.1 to 2 mmol, or 0.1 to 1 mmol, based on 100 g in total of the monomer. When the amount of the reaction product of the organometallic compound and the compound including an alkyl chain having a tertiary amino functional group represented by Chemical Formula 1 falls in the above range, an optimal polymer may be obtained.

In the method of preparing the polymer according to an embodiment of the present invention, the polymerization may be performed with the additional use of a polar additive. The reason why the polar additive is further added is that the reaction rates of the conjugated diene monomer and the aromatic vinyl monomer are controlled by the polar additive.

The polar additive may be a base, or may include ether, amine or mixtures thereof. Specifically, it may be selected from the group consisting of tetrahydrofuran, ditetrahydrofurylpropane, diethylether, cycloamylether, dipropylether, ethylenedimethylether, ethylenedimethylether, diethyleneglycol, dimethylether, tert-butoxyethoxyethane bis(2-dimethylaminoethyl)ether, (dimethylaminoethyl)ethylether, trimethylamine, triethylamine, tripropylamine, and tetramethylethylenediamine, and is preferably ditetrahydropropylpropane, triethylamine, or tetramethylethylenediamine.

The polar additive may be used in an amount of 0.001 to 50 g, 0.001 to 10 g, 0.005 to 1 g, or 0.005 to 0.1 g, based on 100 g in total of the added monomer.

The polar additive may be used in an amount of 0.001 to 10 g, 0.005 to 1 g, or 0.005 to 0.1 g, based on 1 mmol in total of the added reaction product of the organometallic compound and the compound including an alkyl chain having a tertiary amino functional group represented by Chemical Formula 1.

When the conjugated diene monomer and the aromatic vinyl monomer are copolymerized, it is easy to prepare a block copolymer due to the difference in the reaction rates therebetween. However, when the polar additive is added, the low reaction rate of the aromatic vinyl monomer may be increased to thus obtain the microstructure of the corresponding copolymer, for example, a random copolymer.

The polymerization may be exemplified by anionic polymerization. Specifically, the polymerization may be living anionic polymerization in which an active end is obtained through a growth reaction involving anions.

Also, the polymerization may be either high-temperature polymerization or room-temperature polymerization.

High-temperature polymerization is a polymerization process that comprises adding the reaction product of the organometallic compound and the compound including an alkyl chain having a tertiary amino functional group represented by Chemical Formula 1 and then applying heat to increase the reaction temperature, and room-temperature polymerization is a polymerization process that takes place in such a way that heat is not applied after the reaction product of the organometallic compound and the compound including an alkyl chain having a tertiary amino functional group represented by Chemical Formula 1 is added.

The polymerization temperature may be set to −20 to 200° C., 0 to 150° C., or 10 to 120° C.

In an embodiment of the present invention, the method of preparing the conjugated diene-based polymer may be carried out in a batch manner, or alternatively in a continuous manner using at least one reactor.

In addition, the present invention addresses a conjugated diene-based polymer prepared by the above method.

The conjugated diene-based polymer has a number average molecular weight (Mn) of 1,000 to 2,000,000 g/mol, preferably 10,000 to 1,000,000 g/mol, and more preferably 100,000 to 1,000,000 g/mol. When the number average molecular weight of the conjugated diene-based polymer falls in the above range, the modification reaction may efficiently occur, and desired properties may be obtained.

The conjugated diene-based polymer has a molecular weight distribution (Mw/Mn, MWD) of 1 to 10, preferably 1.1 to 5, and more preferably 1.3 to 3. When the molecular weight distribution of the conjugated diene-based polymer falls in the above range, mixing with inorganic particles may be efficiently carried out, thus ensuring desired properties and remarkably increasing processability.

The conjugated diene-based polymer has a vinyl content of 5 wt % or more, preferably 10 wt % or more, and more preferably 15 to 70 wt %.

The vinyl content refers to the amount of a monomer having a vinyl group, or the amount not of 1,4-added conjugated diene monomer but of 1,2-added conjugated diene monomer, based on 100 wt % of the conjugated diene monomer.

When the vinyl content of the conjugated diene-based polymer falls in the above range, the glass transition temperature of the polymer may be elevated. Thus, when such a polymer is applied to tires, the properties required of tires, such as running resistance and braking force, may be satisfied, and superior fuel economy may result.

MODE FOR INVENTION

A better understanding of the present invention may be obtained via the following examples. However, examples of the present invention may be changed in various forms, and are not to be construed as limiting the scope of the present invention.

SYNTHESIS EXAMPLE 1

First Step: Preparation of
1-(diethylaminomethyl)-2,4,6-trimethylbenzene 1-(bromomethyl)-2,4,6-trimethylbenzene (0.5 g, 2.4 mmol) was dissolved in 10 mL of toluene in a 50 mL Schlenk flask, and 3 equivalents of potassium carbonate (0.97 g, 7.0 mmol) and diethylamine (0.52 g, 7.0 mmol) were added and stirred for 20 hr with refluxing. After the reaction, the salt was removed using a glass filter filled with celite. The organic solvent was removed under reduced pressure, yielding 87% (0.42 g) of 1-(diethylaminomethyl)-2,4,6-trimethylbenzene as colorless oil:

$^1$H-NMR (500 MHz, solvent CDCl$_3$): δ ppm 6.82 (1H, s, Ph-H), 3.50 (4H, s, Ph-CH$_2$—N), 2.47 (4H, q, Et-H), 2.37 (6H, s, CH$_3$), 2.26 (3H, s, CH$_3$), 1.01 (6H, t, CH$_3$);

$^{13}$C NMR (125 MHz, solvent CDCl$_3$): δ ppm 138.07 (C-2), 135.89 (C-4,6), 133.14 (C-1,3), 128.82 (C-5), 51.90, 46.23, 20.86, 20.18, 12.10.

Second Step: Preparation of Lithium
1-(diethylaminomethyl)-2,4,6-trimethylbenzene
Initiator The 1-(diethylaminomethyl)-2,4,6-trimethylbenzene was placed in a 50 mL storage flask, and 10 mL of anhydrous n-hexane was added in a nitrogen atmosphere, after which the resulting solution was cooled to −78° C., and 2.5 M n-butyllithium was added dropwise, followed by stirring while the temperature was maintained for 1 hr. Then, the cooling bath was removed, and stirring was performed at room temperature for 2 hr, yielding a pale yellow solution as an initiator.

SYNTHESIS EXAMPLE 2

First Step: Preparation of
1-(diisopropylaminomethyl)-2,4,6-trimethylbenzene

79% (0.60 g) of 1-(diisopropylaminomethyl)-2,4,6-trimethylbenzene was obtained as colorless oil in the same manner as in the First Step of Synthesis Example 1, with the exception that 3 equivalents of diisopropylamine (1.38 mL, 9.9 mmol) were used in lieu of diethylamine:

$^1$H-NMR (500 MHz, solvent CDCl$_3$): δ ppm 6.79 (1H, s, Ph-H), 3.65 (4H, s, Ph-CH$_2$—N), 2.89 (4H, m, iPr-H), 2.38 (6H, s, CH$_3$), 2.24 (3H, s, CH$_3$), 1.03 (24H, d, CH$_3$);

$^{13}$C NMR (125 MHz, solvent CDCl$_3$): δ ppm 138.42 (C-2), 135.61 (C-4,6), 133.46 (C-1,3), 128.95 (C-5), 46.21, 42.69, 20.96, 20.79, 20.36.

Second Step: Preparation of Lithium
1-(diisopropylaminomethyl)-2,4,6-trimethylbenzene
Initiator A pale yellow solution initiator was prepared in the same manner as in the Second Step of Synthesis Example 1, with the exception that 1-(diisopropylaminomethyl)-2,4,6-trimethylbenzene was used as the reactant.

COMPARATIVE SYNTHESIS EXAMPLE 1

First Step: Preparation of
1-(diethylaminomethyl)-2-methylbenzene 1-(bromomethyl)-2-methylbenzene (1.0 g, 8.1 mmol) was dissolved in 20 mL of toluene in a 50 mL Schlenk flask, and 2 equivalents of potassium carbonate (2.24 g, 16.2 mmol) and diethylamine (1.19 g, 16.2 mmol) were added and stirred for 20 hr with refluxing. After the reaction, the salt was removed using a glass filter filled with celite. The organic solvent was removed under reduced pressure, yielding 84% (1.21 g) of 1-(diethylaminomethyl)-2-methylbenzene as colorless oil.

Second Step: Preparation of Lithium
1-(diethylaminomethyl)-2-methylbenzene Initiator The 1-(diethylaminomethyl)-2-methylbenzene was placed in a 50 mL storage flask, and 10 mL of anhydrous n-hexane was added in a nitrogen atmosphere, after which the resulting solution was cooled to −78° C., and 2.5 M n-butyllithium was added dropwise, followed by stirring while the temperature was maintained for 1 hr. Then, the cooling bath was removed, and stirring was performed at room temperature for 2 hr, yielding a pale yellow solution as an initiator.

EXAMPLE 1

6 g of styrene and 44 g of anhydrous n-hexane were added into a 100 mL glass reactor and heated with stirring so that the internal temperature of the reactor was adjusted to 60° C. The initiator (0.5 mmol based on lithium) of Synthesis Example 1 was added into the reactor, followed by an adiabatic heating reaction. After the reaction for 60 min, the reaction was terminated by the addition of 10 mL of methanol into the reactor. The reaction product was reprecipitated in 200 mL of methanol, after which only insoluble solids were dried under reduced pressure, thus obtaining a polymer. The yield was calculated using the amount of the polymer thus obtained. The results of analysis of the polymer are shown in Table 1 below.

EXAMPLE 2

A polymer was prepared in the same manner as in Example 1, with the exception that butadiene (7.5 g), in lieu of styrene, and n-hexane (42.5 g) were used. The results of analysis of the polymer are shown in Table 1 below.

EXAMPLE 3

A polymer was prepared in the same manner as in Example 1, with the exception that styrene (3.0 g), butadiene (7.5 g) and n-hexane (42.5 g) were used. The results of analysis of the polymer are shown in Table 1 below.

COMPARATIVE EXAMPLE 1

A polymer was prepared in the same manner as in Example 1, with the exception that a 2.5 M n-butyllithium hexane solution (0.2 mL, 0.5 mmol) was used as the initiator. The results of analysis of the polymer are shown in Table 1 below.

COMPARATIVE EXAMPLE 2

A polymer was prepared in the same manner as in Example 1, with the exception that a 2.5 M n-butyllithium hexane solution (0.2 mL, 0.5 mmol) was used as the initiator, and butadiene (7.5 g), in lieu of styrene, and n-hexane (42.5 g) were used. The results of analysis of the polymer are shown in Table 1 below.

COMPARATIVE EXAMPLE 3

A polymer was prepared in the same manner as in Example 1, with the exception that a 2.5 M n-butyllithium hexane solution (0.2 mL, 0.5 mmol) was used as the initiator, and styrene (3.0 g), butadiene (7.5 g) and n-hexane (42.5 g) were used. The results of analysis of the polymer are shown in Table 1 below.

COMPARATIVE EXAMPLE 4

A polymer was prepared in the same manner as in Example 1, with the exception that the initiator (0.5 mmol based on lithium) of Comparative Synthesis Example 1 was used. The results of analysis of the polymer are shown in Table 1 below.

COMPARATIVE EXAMPLE 5

A polymer was prepared in the same manner as in Example 1, with the exception that the initiator (0.5 mmol based on lithium) of Comparative Synthesis Example 1 was used, and butadiene (7.5 g), in lieu of styrene, and n-hexane (42.5 g) were used. The results of analysis of the polymer are shown in Table 1 below.

COMPARATIVE EXAMPLE 6

A polymer was prepared in the same manner as in Example 1, with the exception that the initiator (0.5 mmol based on lithium) of Comparative Synthesis Example 1 was used, and styrene (3.0 g), butadiene (7.5 g) and n-hexane (42.5 g) were used. The results of analysis of the polymer are shown in Table 1 below.

Molecular Average Molecular Weight (Mw), Number Average Molecular Weight (Mn), and Molecular Weight Distribution (MWD)

The polymers of Examples 1 to 3 and Comparative Examples 1 to 6 were analyzed through GPC at 40° C. The column herein used was a combination of two PLgel Olexis columns and one PLgel mixed-C column, made by Polymer Laboratories, and all of the replaced columns were mixed bed-type columns. Also, polystyrene (PS) was the GPC standard material for the calculation of molecular weight.

TABLE 1

| | Initiator | Styrene (g) | Butadiene (g) | Yield (%) | GPC (×10³) Mn | MWD |
|---|---|---|---|---|---|---|
| Ex. 1 | Lithium 1-(diethylaminomethyl)-2,4,6-trimethylbenzene | 6 | | 83.7 | 84.3 | 1.314 |
| Ex. 2 | Lithium 1-(diethylaminomethyl)-2,4,6-trimethylbenzene | | 7.5 | 84.0 | 22.6 | 1.177 |
| Ex. 3 | Lithium 1-(diethylaminomethyl)-2,4,6-trimethylbenzene | 3 | 7.5 | 75.1 | 39.9 | 1.225 |
| C. Ex. 1 | n-BuLi | 6 | | 78.7 | 49.7 | 1.377 |
| C. Ex. 2 | n-BuLi | | 7.5 | 75.0 | 23.0 | 1.062 |
| C. Ex. 3 | n-BuLi | 3 | 7.5 | 64.8 | 27.0 | 1.114 |
| C. Ex. 4 | Lithium 1-(diethylaminomethyl)-2-methylbenzene | 6 | | 80.3 | 63.2 | 1.354 |
| C. Ex. 5 | Lithium 1-(diethylaminomethyl)-2-methylbenzene | | 7.5 | 75.0 | 27.8 | 1.125 |
| C. Ex. 6 | Lithium 1-(diethylaminomethyl)-2-methylbenzene | 3 | 7.5 | 70.6 | 32.9 | 1.183 |

In the styrene polymerization of Example 1 using the initiator of Synthesis Example 1 under the same conditions, much higher molecular weight than that of Comparative Example 1 was obtained. In all of the examples using the initiator of Synthesis Example 1, higher yield could be obtained than in the comparative examples. Also, based on the results of comparison testing depending on the number of alkyl chains in the benzene anion (Examples 1, 2, 3 and Comparative Examples 4, 5, 6), as the number of alkyl chains was increased, high yield, high molecular weight, and good molecular weight distribution control resulted.

The invention claimed is:

1. An anionic polymerization initiator, which is a reaction product of an organometallic compound and a compound including an alkyl chain having a tertiary amino functional group
    wherein the compound including an alkyl chain having a tertiary amino functional group is 1-(diethylaminomethyl)-2,4,6-trimethylbenzene or 1-(diisopropylaminomethyl)-2,4,6-trimethylbenzene.

2. The anionic polymerization initiator of claim 1, wherein the organometallic compound is alkyl lithium.

3. A method of preparing a conjugated diene-based polymer, comprising polymerizing a conjugated diene monomer or a conjugated diene monomer and an aromatic vinyl monomer in presence of a solvent using an anionic polymerization initiator, which is a reaction product of an organometallic compound and a compound including an alkyl chain having a tertiary amino functional group represented by Chemical Formula 1 below:

[Chemical Formula 1]

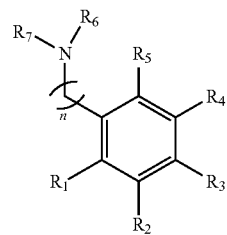

in Chemical Formula 1, $R_1$ to $R_5$ are each independently hydrogen or a C1-C20 hydrocarbon group, two substituents are able to form a single aliphatic or aromatic ring, and at least two of $R_1$ to $R_5$ are alkyl groups;

$R_6$ and $R_7$ are a C1-C14 aliphatic hydrocarbon group or a C5-C14 aromatic hydrocarbon group, two substituents being able to form a single aliphatic or aromatic ring when n is 2 or more; and n is 1 to 12.

4. The method of claim 3, wherein the reaction product of the organometallic compound and the compound including an alkyl chain having a tertiary amino functional group represented by Chemical Formula 1 is used in an amount of 0.01 to 10 mmol based on 100 g in total of the monomer.

5. The method of claim 3, wherein the polymerizing is performed with additional use of a polar additive.

6. The method of claim 5, wherein the polar additive is added in an amount of 0.001 to 10 g based on 1 mmol in total of the reaction product of the organometallic compound and the compound including an alkyl chain having a tertiary amino functional group represented by Chemical Formula 1.

7. A conjugated diene-based polymer, prepared by the method of claim 3.

8. A conjugated diene-based polymer, prepared by the method of claim 4.

9. A conjugated diene-based polymer, prepared by the method of claim 5.

10. A conjugated diene-based polymer, prepared by the method of claim 6.

* * * * *